(12) United States Patent
Wang et al.

(10) Patent No.: US 10,292,759 B2
(45) Date of Patent: May 21, 2019

(54) ELECTROSURGICAL DEVICE FOR VESSEL SEALING

(71) Applicant: Gyrus ACMI, Inc., Southborough, MA (US)

(72) Inventors: Huisun Wang, Maple Grove, MN (US); Kester J. Batchelor, Mound, MN (US)

(73) Assignee: GYRUS ACMI, INC., Southborough, MA (US)

( * ) Notice: Subject to any disclaimer, the term of this patent is extended or adjusted under 35 U.S.C. 154(b) by 375 days.

(21) Appl. No.: 15/181,043

(22) Filed: Jun. 13, 2016

(65) Prior Publication Data
US 2017/0354458 A1 Dec. 14, 2017

(51) Int. Cl.
*A61B 18/14* (2006.01)
*A61B 18/00* (2006.01)
*A61B 17/29* (2006.01)

(52) U.S. Cl.
CPC .. *A61B 18/1445* (2013.01); *A61B 2017/2933* (2013.01); *A61B 2018/0063* (2013.01); *A61B 2018/00077* (2013.01); *A61B 2018/00428* (2013.01); *A61B 2018/00607* (2013.01); *A61B 2018/1452* (2013.01); *A61B 2018/1455* (2013.01)

(58) Field of Classification Search
CPC ...... A61B 2018/00607; A61B 18/1445; A61B 17/295
See application file for complete search history.

(56) References Cited

U.S. PATENT DOCUMENTS

| | | | |
|---|---|---|---|
| 5,443,463 A | 8/1995 | Stern et al. | |
| 6,652,521 B2 | 11/2003 | Schulze | |
| 7,232,440 B2 | 6/2007 | Dumbauld et al. | |
| 7,559,450 B2 | 7/2009 | Wales et al. | |
| 7,744,615 B2 | 6/2010 | Couture | |
| 8,034,056 B2 | 10/2011 | Fencl et al. | |
| 8,968,316 B2 | 3/2015 | Roy et al. | |
| 9,149,326 B2 | 10/2015 | Truckai et al. | |
| 2012/0059375 A1 | 3/2012 | Couture et al. | |
| 2012/0215219 A1* | 8/2012 | Roy | A61B 17/295 606/45 |
| 2014/0031819 A1 | 1/2014 | Dycus et al. | |

* cited by examiner

Primary Examiner — Daniel W Fowler
Assistant Examiner — Rachel A. Vierra

(57) ABSTRACT

An end effector assembly of a forceps includes a first jaw member and a second jaw member. The first jaw member and the second jaw member are selectively positionable relative to one another. At least one of the jaw members includes an electrically conductive tissue engaging surface configured to connect to an electrosurgical energy source, and at least one of the jaw members includes two blade channels defined therein and extending therealong and a feed in member selectively positioned between the two blade channels. The end effector further includes a cutting blade that is translatable such that selective positioning of the feed in member enables the cutting blade to selectively enter into at least one of the two blade channels.

20 Claims, 6 Drawing Sheets

ELECTROSURGICAL DEVICE FOR VESSEL SEALING

FIELD

The present disclosure relates to an electrosurgical device. More specifically, the present disclosure relates to an electrosurgical device for vessel sealing.

BACKGROUND

The statements in this section merely provide background information related to the present disclosure and may not constitute prior art.

Generally forceps may be utilized for laparoscopic surgery. The forceps may be employed to control delicate movements inside a patient and may include a gripping assembly or a cutting assembly. Further, the forceps may utilize electrical energy in the gripping assembly. Typically, the forceps have a pair of opposed resilient jaws that are closed against each other by pulling the jaws into a distal end of a shaft that captures a portion of the jaws that is wider than the distal end opening of the shaft so that the jaws are moved together. Similarly the shaft may be pushed over the jaws so that the jaws are moved together to create a gripping force. In both of these arrangements, the shaft captures the jaws and acts as a cam that forces the jaws together to create the gripping force.

Current bipolar electrosurgical sealing forceps employ a pair of jaws with RF energy to coagulate a vessel and further employ a moveable cutting blade to cut the sealed vessel after coagulation. Conventional vessel sealing procedures generally involve cutting the blood vessels after sealing them. Typically, the vessels connecting the portion of an organ being resected is cut to enable a surgeon to remove the organ from the patient's body. As such, one portion of the cut vessel remains attached to the patient's vascular system, and the other portion of the cut vessel is removed with the organ. After the vessel is sealed and cut, the patient-side of the vessel has to withstand higher blood pressures, and the resected portion of the vessel only has to prevent incidental leakage from the resected organ. Generally, however, vessel sealing devices apply electrosurgical sealing energy equally to both portions of the vessel.

Accordingly, there is a need for a vessel sealing device that provides a better seal on the patient-side of the vessel.

SUMMARY

The present invention provides an end effector for a medical device that has selectable seal widths for vessel sealing.

Accordingly, pursuant to one aspect of the present invention, an end effector assembly of a forceps includes a first jaw member and a second jaw member. The first jaw member and the second jaw member are selectively positionable relative to one another. At least one of the jaw members includes an electrically conductive tissue engaging surface configured to connect to an electrosurgical energy source, and at least one of the jaw members includes two blade channels defined therein and extending therealong and a feed in member selectively positioned between the two blade channels. The end effector further includes a cutting blade that is translatable such that selective positioning of the feed in member enables the cutting blade to selectively enter into at least one of the two blade channels.

The foregoing aspect of the present invention can be further characterized by one or any combination of the features described herein, such as: the source generates electrosurgical energy to coagulate tissue grasped between the first jaw member and the second jaw member; each jaw member includes an electrically conductive tissue engaging surface configured to connect to the electrosurgical energy source; each jaw member includes two blade channels defined therein and extending therealong, the feed in member being positioned between the two blade channels of each jaw member and being selectively positionable to enable the cutting blade to enter at least one of the two blade channels of each jaw member; the cutting blade is positioned offset from a longitudinal axis extending between the two blade channels; the feed in member is an elastic lead member with a first position and a second position, the cutting blade entering into one of the two blade channels when the elastic lead member is in the first position and entering into the other channel when the elastic lead member is in the second position; the elastic lead member is connected to a wire that extends through the at least one jaw member with the two blade channels; and the elastic lead member is in the first position when the wire is relaxed, and the elastic lead member is in the second position when tension is applied to the wire.

Accordingly, pursuant to another aspect of the present invention, a forceps includes an end effector assembly with a first jaw member and a second jaw member. The first jaw member and the second jaw member are selectively positionable relative to one another. At least one of the jaw members includes an electrically conductive tissue engaging surface configured to connect to an electrosurgical energy source, and at least one of the jaw members includes two blade channels defined therein and extending therealong and a feed in member selectively positioned between the two blade channels. The end effector further includes a cutting blade that is translatable such that selective positioning of the feed in member enables the cutting blade to selectively enter into at least one of the two blade channels.

The foregoing aspect of the present invention can be further characterized by one or any combination of the features described herein, such as: the source generates electrosurgical energy to coagulate tissue grasped between the first jaw member and the second jaw member; each jaw member includes an electrically conductive tissue engaging surface configured to connect to the electrosurgical energy source; each jaw member includes two blade channels defined therein and extending therealong, the feed in member being positioned between the two blade channels of each jaw member and being selectively positionable to enable the cutting blade to enter at least one of the two blade channels of each jaw member; the cutting blade is positioned offset from a longitudinal axis extending between the two blade channels; the feed in member is an elastic lead member with a first position and a second position, the cutting blade entering into one of the two blade channels when the elastic lead member is in the first position and entering into the other channel when the elastic lead member is in the second position; the elastic lead member is connected to a wire that extends through the at least one jaw member with the two blade channels; the elastic lead member is in the first position when the wire is relaxed, and the elastic lead member is in the second position when tension is applied to the wire; and the forceps includes a blade mover assembly that is movable between an extended position and a retracted position, the blade mover assembly being configured to translate the cutting blade relative to the at least two blade channels as the blade mover assembly moves between the extended and retracted positions.

Pursuant to yet another aspect of the present invention, a method of using forceps includes one or more of the following steps: opening a first jaw member and a second jaw member of the forceps, the first jaw member and the second jaw member being selectively positionable relative to one another, at least one of the jaw members including an electrically conductive tissue engaging surface configured to connect to an electrosurgical energy source, at least one of the jaw members including two blade channels defined therein and extending therealong and a feed in member positioned between the two blade channels; closing the first jaw member and the second jaw member to grasp tissue therebetween; selectively positioning the feed in member to enable a cutting blade to translate within at least one of the two blade channels; and moving the cutting blade through the at least one of the two blade channels to cut tissue grasped between the first jaw member and the second jaw member.

The method of using the forceps may be further characterized by one or any combination of the following features: generating electrical energy from the electrosurgical energy source to coagulate tissue grasped between the first jaw member and the second jaw member; and the forceps includes a blade mover assembly that is movable between an extended position and a retracted position, wherein the blade mover assembly is configured to translate the cutting blade relative to the at least two blade channels as the blade mover assembly moves between the extended and retracted positions.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings:

FIG. 1 illustrates an electrosurgical forceps in accordance with the principles of the present invention;

FIG. 2 an example of a set of jaws for the forceps shown in FIG. 1;

DETAILED DESCRIPTION

Figure 1:
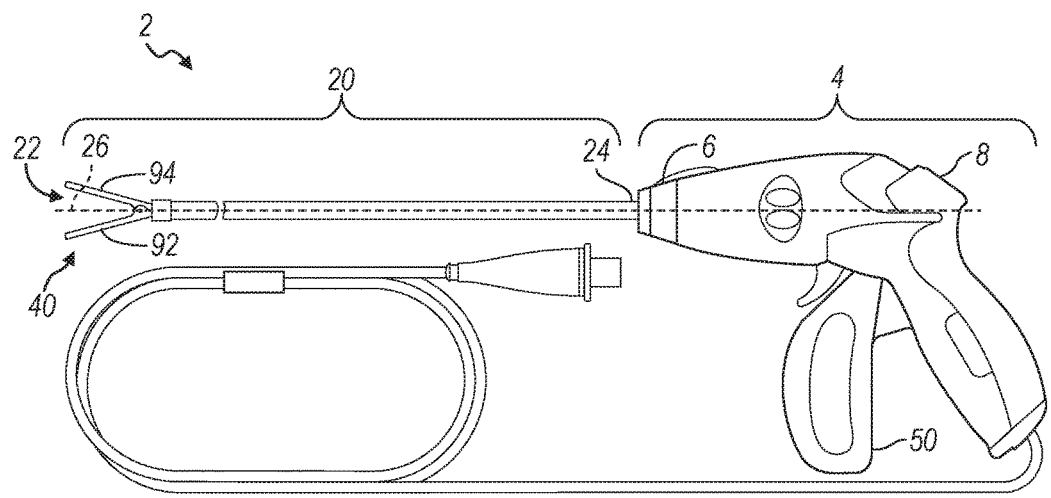

The following description is merely exemplary in nature and is not intended to limit the present disclosure, application, or uses.

Referring now to the drawings, a forceps, such as, for example, a laparoscopic forceps, embodying the principles of the present invention is illustrated therein and designated at 2. The forceps 2 may function to grip an object. The forceps 2 may be used during surgery to grip a feature of interest including: a part of a body, an anatomical feature, tissue, veins, arteries, or a combination thereof. The forceps 2 may function to be used in surgery, for example, laparoscopic surgery. The forceps 2 may be used with or without power. Current may be passed through the forceps 2 so that the forceps are used for electrosurgery. For example, a therapy current may be passed from one jaw to a second jaw when tissue is located within the jaw and the therapy current may coagulate blood, cauterize, cut, or a combination thereof. The forceps 2 may generally include one or more working assemblies and sufficient controls to work the one or more assemblies. The forceps 2 may include parts employed to perform the recited functions and may include generally, a stylet (e.g., a tubular member, a hollow tube, or an assembly of tubes), a hand piece, one or more operable mechanisms used to actuate the stylet, or a combination thereof. The hand piece may be an assembly of parts or housing structures capable of forming a hand piece structure with a cavity. Note that the present invention is not limited to laparoscopic procedures. That is, the below described jaws can be employed with any type of medical device that clamps onto tissue.

Turning now to FIG. 1, a side view of the forceps 2 is shown. The forceps 2 include a handpiece 4 having a distal end 6 and a proximal end 8. The handpiece 4 also includes at least one operable mechanism 50. A tubular member 20 has a proximal end 24 that is connected to the distal end 6 of the handpiece 4. The tubular member 20 includes a distal end 22 that includes jaws 40 extending therefrom. The jaws 40 have members 92 and 94 that open and close when the tubular member 20 is moved forward along the longitudinal axis 26 of the tubular member into contact with the members 92 and 94 or the jaws 40 are moved backwards along the longitudinal axis 26 into contact with the tubular member 20.

Figure 2:
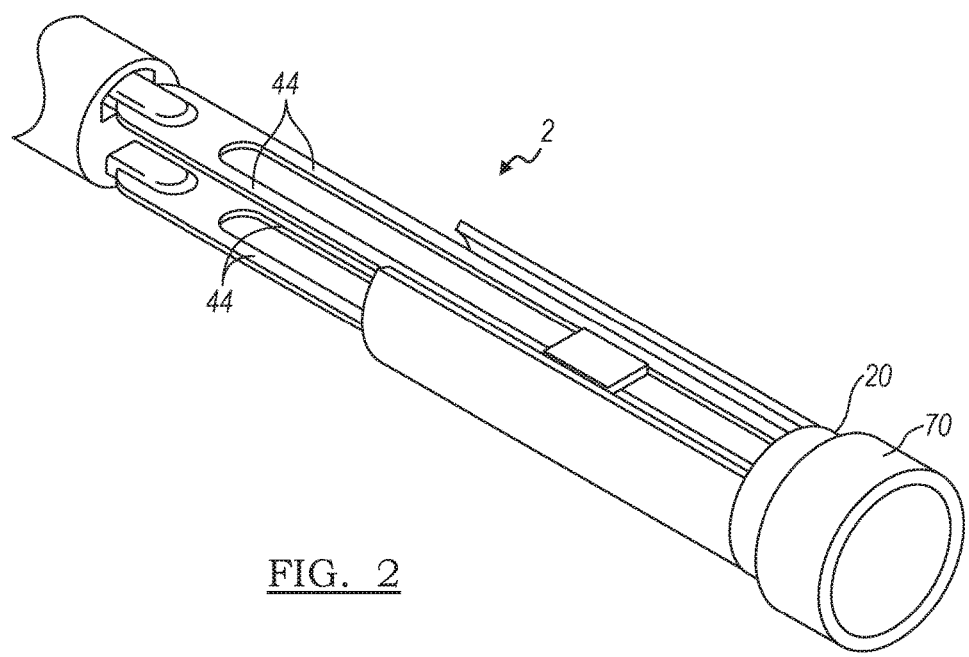
Figure 6:
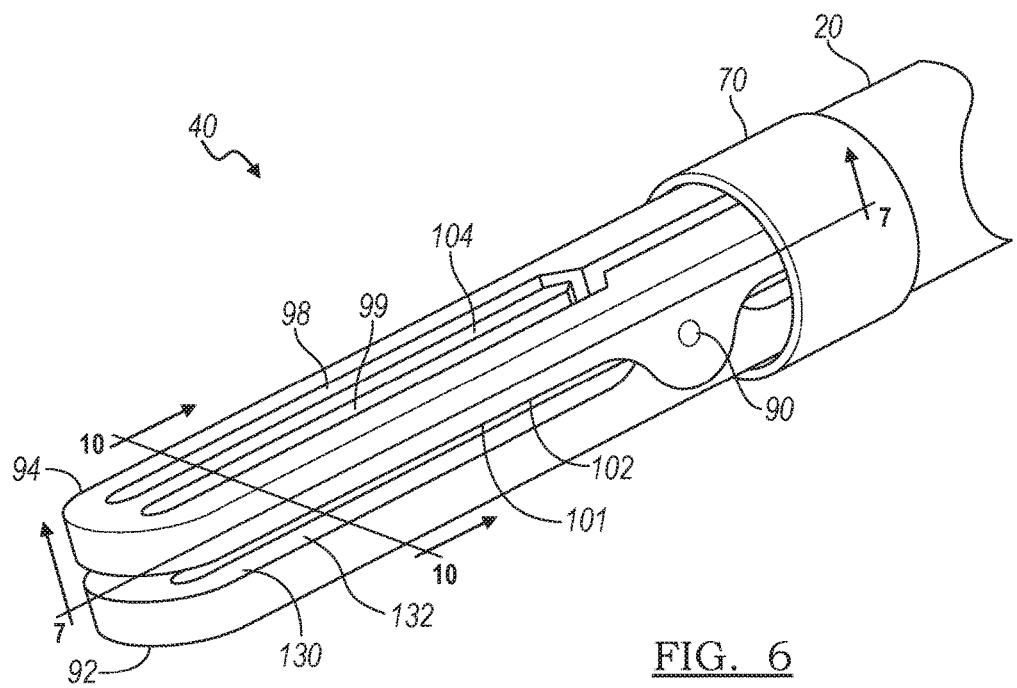
FIG. 6 illustrates a perspective view of the forceps shown in FIG. 1.
Figure 7:
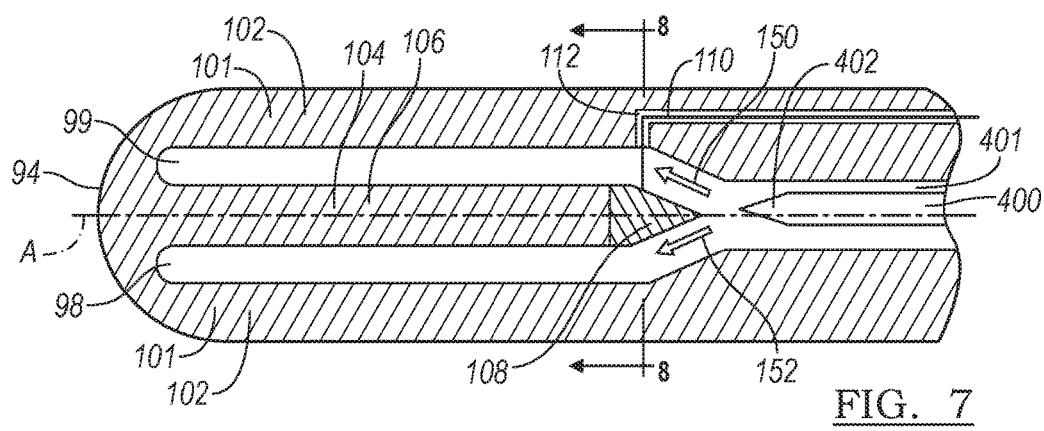
FIG. 7 illustrates an interior view of the upper jaw taken along the line 7-7 of FIG. 6.
Figure 8:
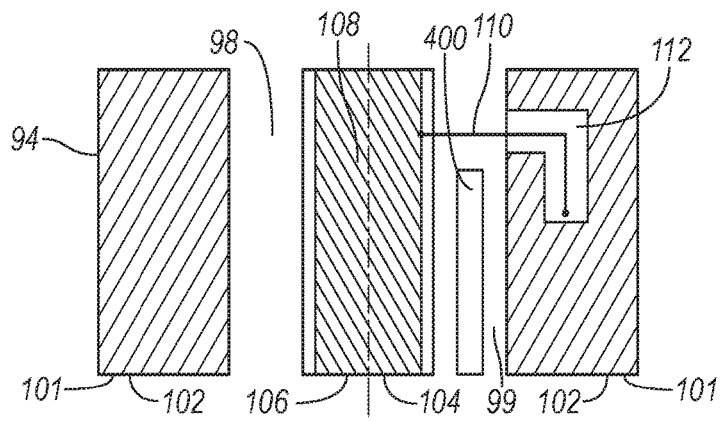
FIG. 8 illustrates a cross-sectional view of the jaw taken along the line 8-8 of FIG. 7.
Figure 10:
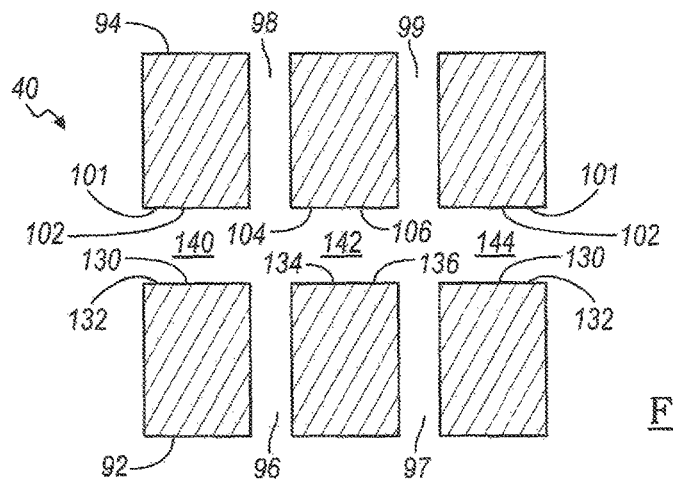
FIG. 10 illustrates a cross-sectional view of the jaws taken along the line 10-10 of FIG. 6.

Referring further to FIGS. 2, 6 and 10, a camming shaft 70 is located on the forceps 2 with the jaws 40 extending therefrom. The members 92 and 94 are biased by the camming shaft 70 so that the jaws 40 are opened and closed. The member 94 includes lateral portions 101 and a medial or center portion 104. A pair of channels or slots 98 and 99 extends substantially between the lateral portions 101 and the medial portion 104. The lateral portions 101 include sealing surfaces 102 and the medial portion 104 includes a sealing surface 106. The member 92 includes lateral portions 130 and a medial or center portion 134. A pair of channels or slots 96 and 97 extends substantially between the lateral portions 130 and the medial portion 134. The lateral portions 130 include sealing surfaces 132 and the medial portion 134 includes a sealing surface 136.

Figure 3:
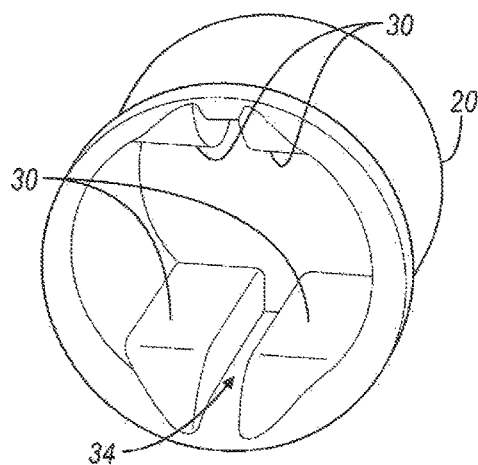
FIG. 3 illustrates an end of a tubular member and/or a camming shaft for the forceps.

FIG. 3 illustrates the end of the tubular member 20 or a camming shaft showing a pair of internal flat portions 30 along the top surfaces and the bottom surfaces. A blade recess 34 extends between the pair of internal flat portions 30 so that a blade 400 (FIGS. 12 and 13) extends out of the tubular member 20.

Figure 4:
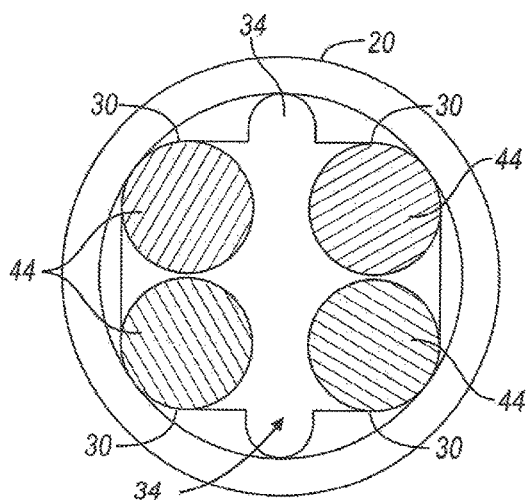
FIG. 4 illustrates an end view of a tubular member and/or a camming shaft.

FIG. 4 illustrates a cross-sectional view of a tubular member 20. The internal flat portions 30 include at least a portion that has a complementary shape to that of the legs of the jaws 44 (see also FIG. 2). Accordingly, as the tubular member 20 or the legs 44 axially move, the internal flat portions 30 control the orientation and movement of the jaws.

Figure 5:
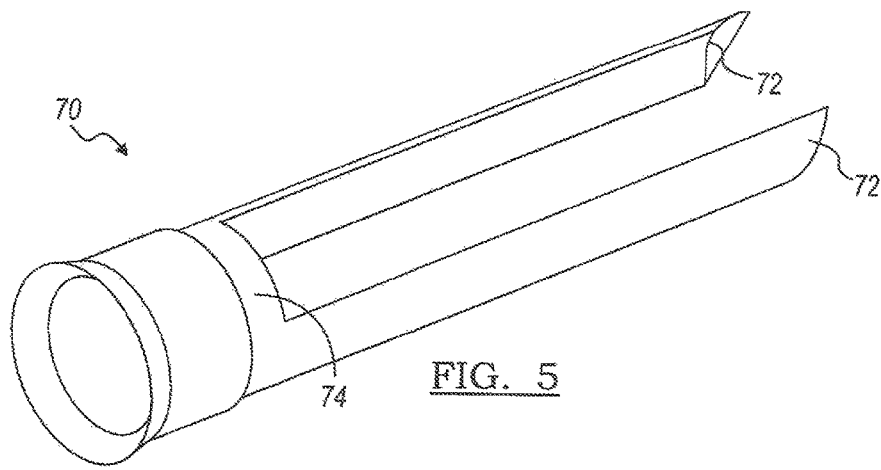
FIG. 5 illustrates a perspective view of a camming shaft.

FIG. 5 illustrates a perspective view of one example of a camming shaft 70 that is inserted into the tubular member 20. The camming shaft 70 includes a molded flare 74 with a pair of protrusions 72 extending therefrom.

FIG. 6 further illustrates the jaws 40 including a pin 90 located between the jaws. The pin 90 holds the jaw members 92 and 94 together and provide a pivot point for the jaw members 92 and 94 such that the members 92 and 94 close when the tubular member 20 is slid over the opposing members 92 and 94.

Referring further to FIGS. 7, 8, 15 and 16, the center portion 104, as well as the center portion 134 of the jaw member 92, includes an elastic feed in member 108. The elastic feed in member 108 is connected to a wire 110 that extends through a channel 112 of one of the lateral portions 101 of the jaw member 94. The wire 110 may further extend through the tubular member 20 to an actuator in the handpiece 4 which can be operated by a medical professional to deflect the position of the elastic feed in member 108. The blade 400 is slightly offset from a centerline A that extends through the medial portions 104 and 134 of the jaw members 92 and 94. The elastic feed in member 108 is positioned selectively to enable the blade 400 to enter a selected slots 96, 98 or 97, 99. More specifically, after the jaw members 92 and 94 are in a closed positioned and when the wire 110 is relaxed, the elastic feed in member 108 deflects the end of the blade 402 into the slots 97 and 99 so that the blade 400 is able to reciprocate in the blade channel 400 and the slots 97 and 99 in a first position as indicated by the arrow 150. When the wire 110 is pulled to produce tension in the wire 110 to sufficiently move the elastic feed in member 108, the elastic feed in member 108 deflects the end of the blade 402 into the slots 96 and 98 so that the blade 400 is able to reciprocate in the blade channel 400 and the slots 96 and 98 in a second position as indicated by the arrow 152. The elastic feed in member 108 can be made from an elastomer or any other suitable material that returns to its original position when the wire 110 is relaxed.

As shown specifically in FIG. 10, when the jaw members 92 and 94 are closed together to clamp on a vessel, the lateral sealing surfaces 102 and 130 adjacent the slots 98 and 96, respectively, form a first compression zone 140, the medial sealing surfaces 106 and 136 form a second compression zone 142, and the lateral sealing surfaces 102 and 130 adjacent the slots 99 and 97, respectively, form a third compression zone 144.

In various arrangements, the jaw members 92 and 94 can be electrical connected to a generator that provides a source of electrosurgical energy so that a RF voltage with different potentials can be applied to the electrically connected sections of the jaw members 92 and 94. The RF voltage produces a current that passes from one jaw member to the other jaw member electrode through tissue, thereby heating the tissue to coagulate or cut the tissue.

Figure 9:
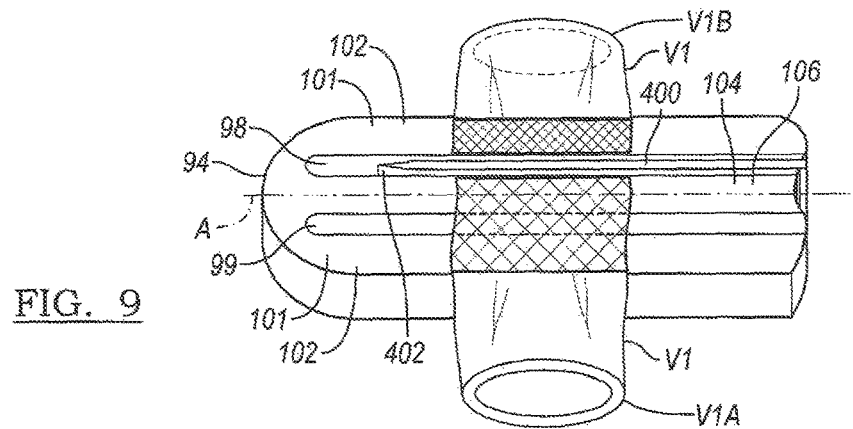
FIG. 9 illustrates the cutting of a vessel.

Hence, as shown in FIG. 9, a portion V1A of the vessel V1 is sealed by the first and the second compression zones 140 and 142 and a portion V1B of the vessel V1 is sealed by the third compression zone 144 when the blade 400 reciprocates along the slots 97 and 99. Similarly, the portion V1A of the vessel V1 is sealed by the first compression zone 140 and the portion V1B of the vessel V1 is sealed by the second and the third compression zones 142 and 144 when the blade reciprocates along the slots 96 and 98. The portion V1A or V1B sealed by two compression zones has a wider seal width to withstand higher blood pressures than the portion sealed with one compression zone which produces a narrow seal width.

The ability of the set of jaws 40 to provide different sealing widths is beneficial, for example, during the resection of an organ from a patient. During such a surgical procedure, one portion of the cut vessel remains attached to the patient's vascular system, and the other portion of the cut vessel is removed with the organ. The use of the jaws 40 enables sealing the patient-side of the vessel with a wider seal width to withstand higher blood pressures, and sealing the resected portion of the vessel with a narrower seal width to prevent incidental leakage from the resected organ.

Figure 11:
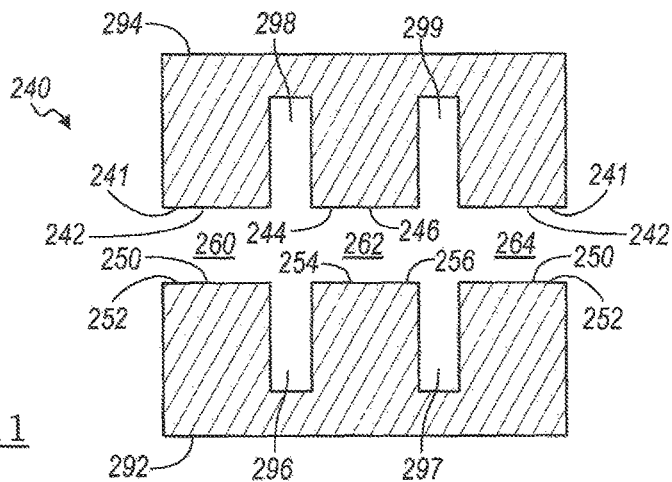
FIG. 11 illustrates a cross-sectional view of another set of jaws in accordance with the principles of the present invention.

Referring now to FIG. 11, there is shown a cross-sectional view of another set of jaws 240 in accordance with the principles of the present invention. The member 294 includes lateral portions 241 and a medial or center portion 244. A pair of channels or slots 298 and 299 extends substantially between the lateral portions 241 and the medial portion 244. The lateral portions 241 include sealing surfaces 242 and the medial portion 244 includes a sealing surface 246. The member 292 includes lateral portions 250 and a medial or center portion 254. A pair of channels or slots 296 and 297 extends substantially between the lateral portions 250 and the medial portion 254. The lateral portions 250 include sealing surfaces 252 and the medial portion 254 includes a sealing surface 256. Unlike the slots 96, 97, 98 and 99 of the jaws 40, the slots 296, 297, 298 and 299 of the jaws 240 do not traverse entirely through the jaw members.

When the jaw members 292 and 294 are closed together to clamp onto a vessel, the lateral sealing surfaces 242 and 252 adjacent the slots 298 and 296, respectively, form a first compression zone 260, the medial sealing surfaces 246 and 256 form a second compression zone 262, and the lateral sealing surfaces 242 and 252 adjacent the slots 299 and 297, respectively, form a third compression zone 264. Other features of the jaw 240 are identical to those of the jaw 40, in particular, the operation of the elastic feed in member 108 with the wire 110. Hence, the blade 400 can be selectively directed into the slots 296, 298 or the slots 297, 299.

In various arrangements, the jaw members 292 and 294 can be electrical connected to a generator that provides a source of electrosurgical energy so that a RF voltage with different potentials can be applied to the electrically connected sections of the jaw members 292 and 294. The RF voltage produces a current that passes from one jaw member to the other jaw member electrode through tissue, thereby heating the tissue to coagulate or cut the tissue. Accordingly, a first portion of a vessel clamped by the jaw members 292 and 294 is sealed by the first and the second compression zones 240 and 262 and a second portion of the vessel is sealed by the third compression zone 264 when the blade 400 reciprocates along the slots 297 and 299. Similarly, the first portion of the vessel is sealed by the first compression zone 260 and the second portion of the vessel is sealed by the second and the third compression zones 262 and 264 when the blade reciprocates along the slots 296 and 298. Again, the portion sealed by two compression zones has a wider seal width to withstand higher blood pressures than the portion sealed with one compression zone which produces a narrow seal width.

Figure 12:
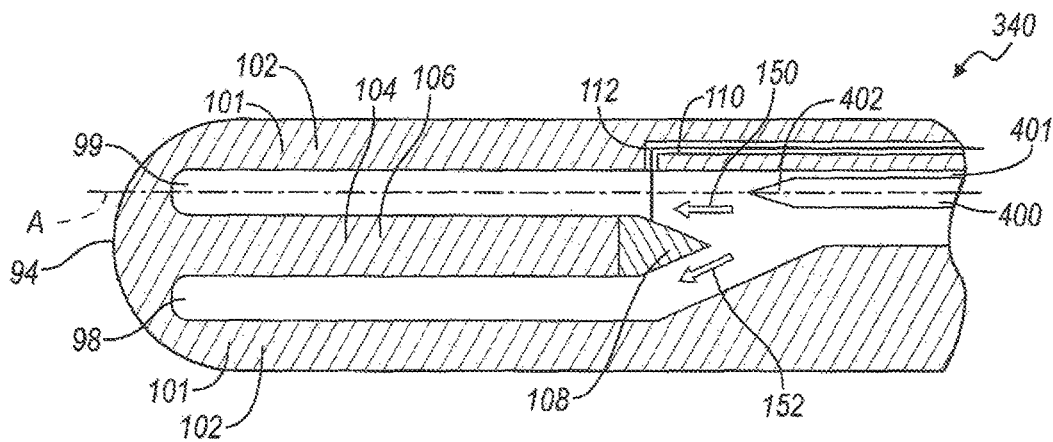
FIG. 12 illustrates an interior view of another jaw in accordance with the principles of the present invention.

Referring now to FIG. 12, there is shown an interior view of the upper jaw member 94 in an alternative jaw arrangement 340. The features of the jaw arrangement 340 are similar to those described in relation to the jaw arrangement 40, and, therefore, similar features are identified by the same reference numbers. Moreover, the lower jaw member 92 is a mirror image of the upper jaw member 94. A particular feature of the jaw arrangement 340 that is different than the jaw arrangement 40 is the positioning of the blade 400 and the blade channel 401. In the jaw arrangement 340, the blade 400 and the blade channel 401 are aligned with a centerline A that extends through the slot 99 (and hence slot 97 of the lower jaw 92). Therefore, when the tension in the wire 110 is relaxed, the blade 400 is able to reciprocate in the slots 97, 99 and 401 as indicated by the arrow 150. And when the wire 110 is pulled to move the elastic feed in member 108 upwards, the elastic feed in member 108 deflects the blade 400 into the slots 96, 98 as indicated by the arrow 152.

Figure 13:
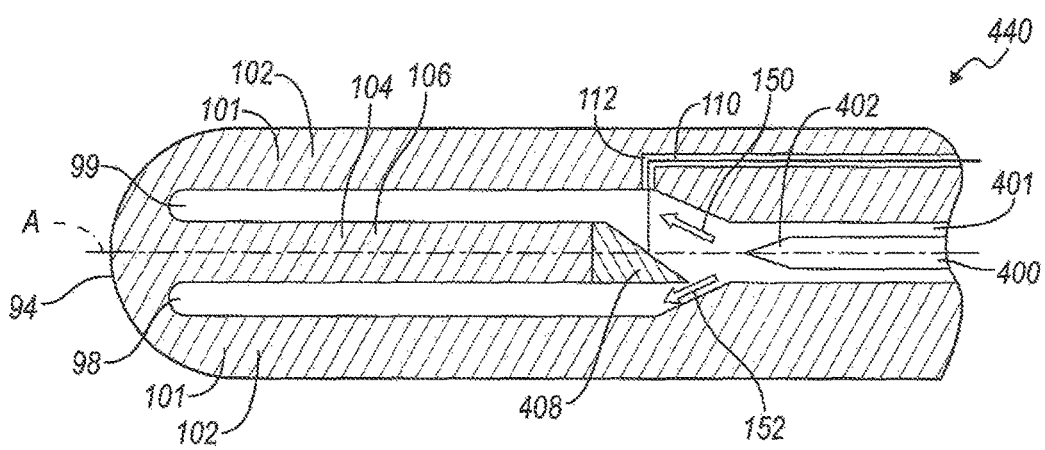
FIG. 13 illustrates an interior view of yet another jaw in accordance with the principles of the present invention.

Referring to FIG. 13, there is shown an interior view of the upper jaw member 94 in yet another alternative jaw arrangement 440. Again, the features of the jaw arrangement 440 are similar to those of the jaw arrangement 40, and the lower jaw member 92 mirrors the upper jaw member 94. In the jaw arrangement 440, however, the blade 400 is aligned (that is, not offset) from the centerline A extending through the medial portions 104 and 134, and the feed in member 108 has been replaced with an asymmetric feed in member 408 with a tip that is offset from the centerline A. Hence, the asymmetric shape of the feed in member 408 deflects the blade 400 into the slots 97, 99 when the wire 110 is relaxed. And when the wire 110 is pulled so that the tip of the feed in member 408 moves past the centerline A, the feed in member 408 deflects the blade 400 into the slots 96 and 98.

Figure 14:
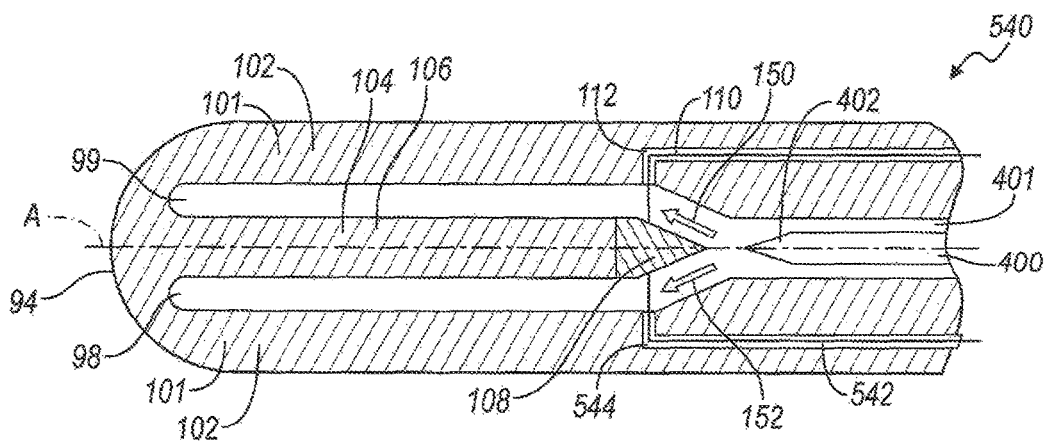
FIG. 14 illustrates an interior view of yet another jaw in accordance with the principles of the present invention.

Referring to FIG. 14, there is shown an interior view of the upper jaw member 94 in yet another alternative arrangement 540. The features of the jaw member 94, as well as the jaw member 92, of the jaw arrangement 540 are similar to those of the jaw arrangement 40 and are, therefore, identified by the same reference numbers. In the jaw arrangement 540, both the medial portions 104 and 134 and the blade 400 are aligned with the centerline A. The jaw arrangement 540 includes an additional wire 542 that extends through a channel 544 in the jaw member 94. Accordingly, pulling the wire 110 enables the blade 400 to reciprocate in the slots 97, 99, while pulling the wire 542 enables the blade 400 to reciprocate in the slots 96, 98. The pull wire 544 may further extend through the tubular member 20 to an actuator in the handpiece 4 which can be operated by a medical professional to deflect the position of the elastic feed in member 408.

Note that in the aforementioned jaw arrangements 40, 240, 340, 440 and 540, the wires 110 and 542 are generally described as wires that are pulled to deflect the feed in members 108 or 408. In certain arrangements, however, the wires 110 and 542 can be stiff enough to enable pushing the wire against the respective elastic feed in member 108 or 408 to deflect the member. Hence, in such arrangements the wire 110 or 542 or each wire can be both a pull wire and a push wire.

Figure 15:
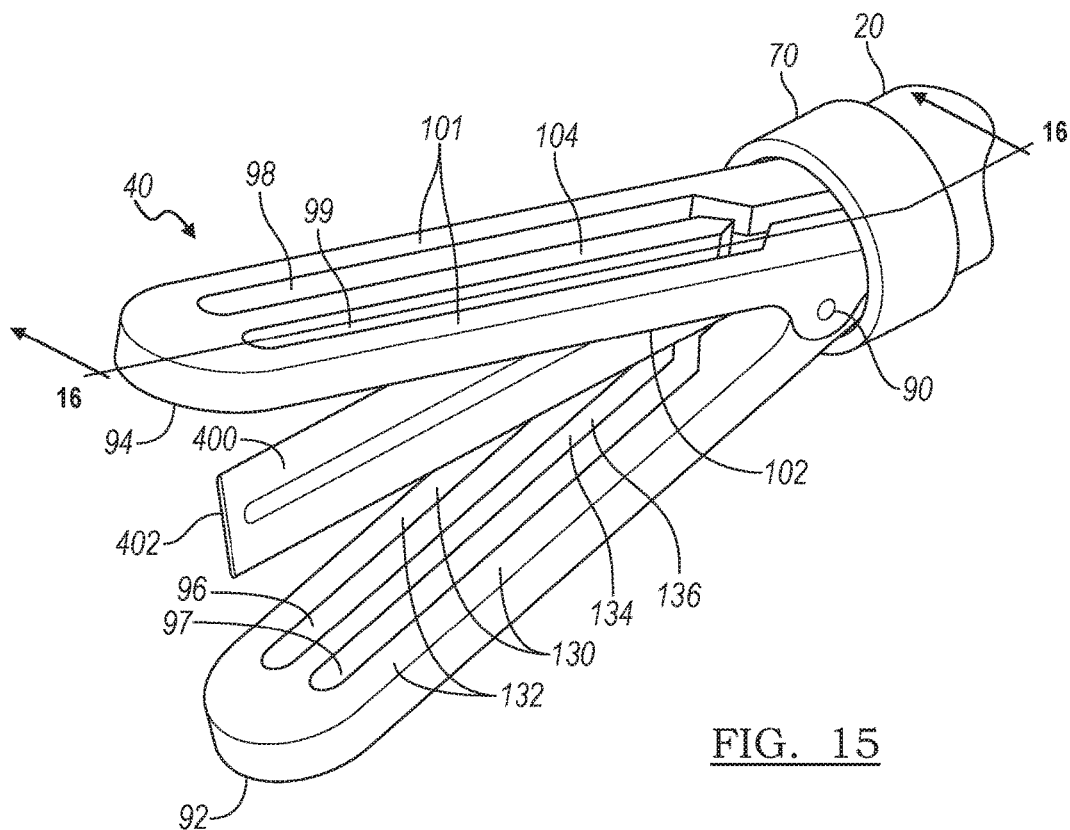
FIG. 15 illustrates a perspective view of the jaws shown in FIG. 6 with a cutting blade.
Figure 16:
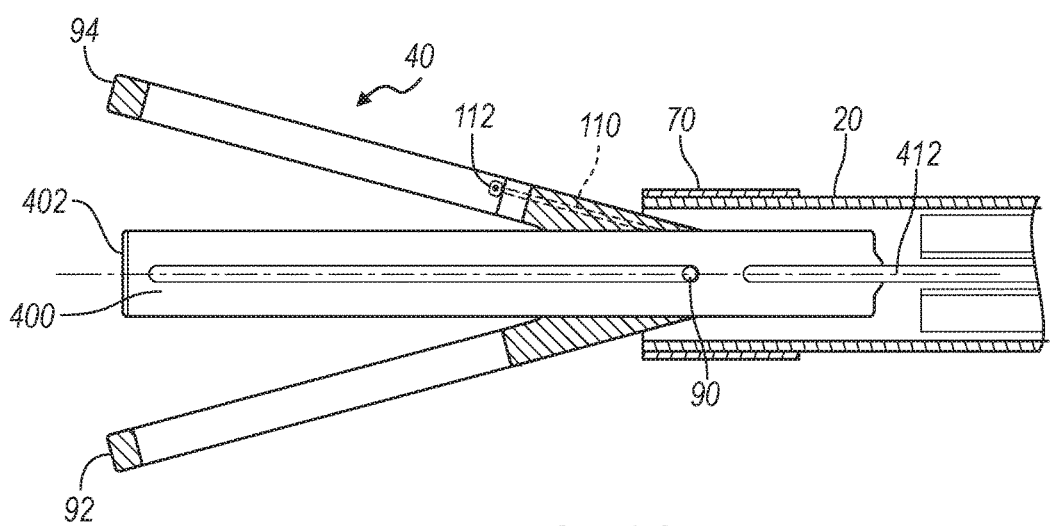
FIG. 16 illustrates a side view of the jaws shown in FIG. 6 with the cutting blade.

As described previously, the jaws 40 include the blade 400. As shown in FIGS. 15 and 16, the blade 400 includes a slot 402 that engages with the pin 90 to allow the blade 400 to reciprocate along the pin 90. The blade 400 is connected to a blade mover assembly including a blade shaft 412. Hence, axial movement of the blade shaft 412 results in reciprocating axial movement of the blade 400 along the slots 96 and 98 in the second position or slots 97 and 99 in the first position to cut tissue clamped between the jaw members 92 and 94. A similar blade mover assembly arrangement can be incorporated to the jaws 240, 340, 440, and 540.

The description of the invention is merely exemplary in nature and variations that do not depart from the gist of the invention are intended to be within the scope of the invention. Such variations are not to be regarded as a departure from the spirit and scope of the invention.

What is claimed is:

1. An end effector assembly of a forceps comprising:
a first jaw member;
a second jaw member, the first jaw member and the second jaw member being selectively positionable relative to one another, at least one of the jaw members including an electrically conductive tissue engaging surface configured to connect to an electrosurgical energy source, at least one of the jaw members including two blade channels defined therein and extending therealong and a feed in member positioned between the two blade channels, the feed in member being selectively positionable; and
a cutting blade that is translatable such that selective positioning of the feed in member enables the cutting blade to selectively enter into at least one of the two blade channels.

2. The end effector assembly of claim 1 wherein the source generates electrosurgical energy to coagulate tissue grasped between the first jaw member and the second jaw member.

3. The end effector assembly of claim 2 wherein each jaw member includes an electrically conductive tissue engaging surface configured to connect to the electrosurgical energy source.

4. The end effector assembly of claim 1 wherein each jaw member includes two blade channels defined therein and extending therealong, the feed in member being positioned between the two blade channels of each jaw member and being selectively positionable to enable the cutting blade to enter at least one of the two blade channels of each jaw member.

5. The end effector assembly of claim 1 wherein the cutting blade is positioned offset from a longitudinal axis extending between the two blade channels.

6. The end effector assembly of claim 1 wherein the feed in member is an elastic lead member with a first position and a second position, the cutting blade entering into one of the two blade channels when the elastic lead member is in the first position and entering into the other channel when the elastic lead member is in the second position.

7. The end effector assembly of claim 6 wherein the elastic lead member is connected to a wire that extends through the at least one jaw member with the two blade channels.

8. The end effector assembly of claim 7 wherein the elastic lead member is in the first position when the wire is relaxed, and wherein the elastic lead member is in the second position when tension is applied to the wire.

9. A forceps comprising:
  at least one shaft that includes an end effector assembly at a distal end thereof, the end effector assembly including:
  a first jaw member;
    a second jaw member, the first jaw member and the second jaw member being selectively positionable relative to one another, at least one of the jaw members including an electrically conductive tissue engaging surface configured to connect to an electrosurgical energy source, at least one of the jaw members including two blade channels defined therein and extending therealong and a feed in member positioned between the two blade channels, the feed in member being selectively positionable; and
    a cutting blade that is translatable such that selective positioning of the feed in member enables the cutting blade to selectively enter into at least one of the two blade channels.

10. The forceps of claim 9 wherein the source generates electrosurgical energy to coagulate tissue grasped between the first jaw member and the second jaw member.

11. The forceps of claim 10 wherein each jaw member includes an electrically conductive tissue engaging surface configured to connect to the electrosurgical energy source.

12. The forceps of claim 9 wherein each jaw member includes two blade channels defined therein and extending therealong, the feed in member being positioned between the two blade channels of each jaw member and being selectively positionable to enable the cutting blade to enter at least one of the two blade channels of each jaw member.

13. The forceps of claim 9 wherein the cutting blade is positioned offset from a longitudinal axis extending between the two blade channels.

14. The forceps of claim 9 wherein the feed in member is an elastic lead member with a first position and a second position, the cutting blade entering into one of the two blade channels when the elastic lead member is in the first position and entering into the other channel when the elastic lead member is in the second position.

15. The forceps of claim 14 wherein the elastic lead member is connected to a wire that extends through the at least one jaw member with the two blade channels.

16. The forceps of claim 15 wherein the elastic lead member is in the first position when the wire is relaxed, and wherein the elastic lead member is in the second position when tension is applied to the wire.

17. The forceps of claim 9 further comprising a blade mover assembly that is movable between an extended position and a retracted position, wherein the blade mover assembly is configured to translate the cutting blade relative to the at least two blade channels as the blade mover assembly moves between the extended and retracted positions.

18. A method of using forceps, the method comprising:
  opening a first jaw member and a second jaw member of the forceps, the first jaw member and the second jaw member being selectively positionable relative to one another, at least one of the jaw members including an electrically conductive tissue engaging surface configured to connect to an electrosurgical energy source, at least one of the jaw members including two blade channels defined therein and extending therealong and a feed in member positioned between the two blade channels;
  closing the first jaw member and the second jaw member to grasp tissue therebetween;
  selectively positioning the feed in member to enable a cutting blade to translate within at least one of the two blade channels; and
  moving the cutting blade through the at least one of the two blade channels to cut tissue grasped between the first jaw member and the second jaw member.

19. The method of claim 18 further comprising generating electrical energy from the electrosurgical energy source to coagulate tissue grasped between the first jaw member and the second jaw member.

20. The method of claim 18 wherein the forceps includes a blade mover assembly that is movable between an extended position and a retracted position, wherein the blade mover assembly is configured to translate the cutting blade relative to the at least two blade channels as the blade mover assembly moves between the extended and retracted positions.

* * * * *